United States Patent
Sagol et al.

(10) Patent No.: US 10,040,786 B2
(45) Date of Patent: Aug. 7, 2018

(54) PROCESS FOR PREPARING A POLYMORPH OF RIVAROXABAN

(71) Applicant: Zaklady Farmaceutyczne Polpharma SA, Starogard Gdanski (PL)

(72) Inventors: Karol Sagol, Tczew (PL); Magdalena Kozien-Sajnog, Cracow (PL)

(73) Assignee: ZAKLADY FARMACEUTYCZNE POLPHAMRA SA (PL)

(*) Notice: Subject to any disclaimer, the term of this patent is extended or adjusted under 35 U.S.C. 154(b) by 0 days.

(21) Appl. No.: 15/520,499

(22) PCT Filed: Oct. 22, 2015

(86) PCT No.: PCT/EP2015/074538
§ 371 (c)(1),
(2) Date: Apr. 20, 2017

(87) PCT Pub. No.: WO2016/062828
PCT Pub. Date: Apr. 28, 2016

(65) Prior Publication Data
US 2017/0313689 A1  Nov. 2, 2017

(30) Foreign Application Priority Data
Oct. 22, 2014  (EP) .................................. 14460075

(51) Int. Cl.
C07D 413/14 (2006.01)
C07D 265/32 (2006.01)
C07D 333/38 (2006.01)
C07D 413/12 (2006.01)

(52) U.S. Cl.
CPC ......... *C07D 413/14* (2013.01); *C07D 265/32* (2013.01); *C07D 333/38* (2013.01); *C07D 413/12* (2013.01)

(58) Field of Classification Search
CPC .................................................. C07D 413/14
See application file for complete search history.

(56) References Cited

U.S. PATENT DOCUMENTS

2010/0152189 A1   6/2010   Grunenberg et al.

FOREIGN PATENT DOCUMENTS

| WO | 2007/039132 A1 | 4/2007 |
| WO | 2011/012321 A1 | 2/2011 |
| WO | 2014/096214 A1 | 6/2014 |
| WO | 2015/111076 A2 | 7/2015 |

OTHER PUBLICATIONS

International Search Report for corresponding application No. PCT/EP2015/074538 dated Dec. 12, 2015.
West H., "Crystalline form of 4-{4-[(5S)-5-(aminomethyl)-2-oxo-1,3-oxazolidin-3-yl]phenyl}morpholin-3-one hydrochloride and crystalline forms of S-enantiomer and of racemic 5-Chloro-N-({2-oxo-3-[4-(3-oxo-4-morpholinyl)phenyl]-1,3-oxazolidin-5-yl}methyl)-2-thiophene-carboxamide" IP.Com Journal, IP.Com Inc., NY, US, Aug. 5, 2010 XP013143681.
Anil C Mali et al., "Facile approach for the synthesis of rivaroxaban using alternate synthon: reaction, crystallization and isolation in single pot to achieve desired yield, quality and crystal form", Sustatainable Chemical Processes, vol. 48, No. 1, Jul. 13, 2015, p. 5900, XP055230109.

*Primary Examiner* — Rebecca L Anderson
(74) *Attorney, Agent, or Firm* — Wood, Phillips, Katz, Clark & Mortimer

(57) ABSTRACT

This invention describes a process for the preparation of rivaroxaban modification I comprising: (i) dissolving rivaroxaban in a mixture of a solvent (e.g. THF) and an antisolvent (e.g. water and/or toluene), wherein the antisolvent has a higher boiling point than the solvent; (ii) removing the solvent by distillation; and (iii) collecting the resultant rivaroxaban modification I.

13 Claims, 4 Drawing Sheets

PROCESS FOR PREPARING A POLYMORPH OF RIVAROXABAN

FIELD OF THE INVENTION

The present invention relates to a crystallisation process, and more specifically to the preparation of rivaroxaban crystalline modification I.

BACKGROUND OF THE INVENTION

Rivaroxaban is named (S)-5-chloro-N-{[2-oxo-3-[4-(3-oxomorpholin-4-yl)phenyl]-1,3-oxazolidin-5-yl]methyl}-2-thiophene-carboxamide and has the following structure:

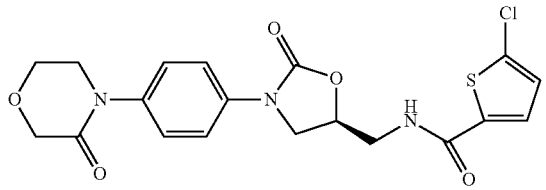 [SMILES: O=C(NC[C@H]1CN(c2ccc(N3CCOCC3=O)cc2)C(=O)O1)c1ccc(Cl)s1]

Rivaroxaban is a direct factor Xa inhibitor ("xaban"). It acts directly upon Factor X in the coagulation cascade and hence may be used as an anticoagulant. It is marketed in a number of countries as Xarelto® as an oral anticoagulant. It has been indicated for the treatment of various thromboembolic diseases, see, for example, WO 01/47949 (the basic patent), WO 2004/060887 and WO 2007/039132.

Rivaroxaban may be prepared according to the procedures described in WO 01/47949 and WO 2004/060887. Rivaroxaban is obtained in WO 01/47949 as crystalline modification I by purifying the crude product using column chromatography with a dichloromethane/methanol eluent. It is further discussed in WO 2007/039132. Modification I has a melting point of approximately 230° C. and a characteristic DSC, X-ray powder diffractogram, IR spectrum, Raman spectrum, FIR spectrum and NIR spectrum as set out in FIGS. 1-6 of WO 2007/039132.

The characterising peaks are reported as follows.
XRPD 2θ (°): 8.9, 12.0, 14.3, 16.5, 17.4, 18.1, 19.5, 19.9, 21.7, 22.5, 23.4, 24.1, 24.5, 24.7, 25.6, 26.4, 26.7, 30.0, 30.1 and 31.8.
IR (cm$^{-1}$): 564, 686, 708, 746, 757, 830, 846, 920, 991, 1011, 1056, 1077, 1120, 1146, 1163, 1219, 1286, 1307, 1323, 1341, 1374, 1411, 1429, 1470, 1486, 1517, 1546, 1605, 1646, 1669, 1737, 2867, 2895, 2936, 2976 and 3354.
Raman (cm$^{-1}$): 84, 111, 642, 672, 687, 745, 779, 792, 1083, 1099, 1232, 1280, 1307, 1325, 1343, 1428, 1473, 1485, 1548, 1605, 1638, 1664, 1722, 2899, 2944, 2983 and 3074.
FIR (cm$^{-1}$): 82, 97, 138, 169, 179, 210, 226, 247, 272, 283, 298, 303, 350, 394, 417, 438, 458, 475 and 484.
NIR (cm$^{-1}$): 4082, 4142, 4170, 4228, 4299, 4376, 4429, 4479, 4633, 4791, 4877, 4907, 5081, 5760, 5885, 6002, 6441, 6564, 8473 and 8833.

A drawback of the procedures set out in WO 01/47949 and WO 2004/060887 is that column chromatography is required to prepare modification I. This is not a useful technique for scaling up the procedure. WO 2005/068456 discloses a purification of rivaroxaban by recrystallising from acetic acid. However, the polymorphic form is not reported. Moreover, acetic acid is difficult to remove from the final product and reacts with rivaroxaban on storage to produce undesirable impurities in the product.

WO 2007/039132 discloses other techniques for the purification of rivaroxaban, but these do not form the required modification I. The products are other solid state forms, including modification II, modification III, an amorphous form, a hydrate form, an NMP solvate and an inclusion compound with THF.

There remains a need in the art for a more efficient process for the preparation of modification I.

BRIEF SUMMARY OF THE INVENTION

Accordingly, the present invention provides a process for the preparation of rivaroxaban modification I comprising:
(i) dissolving rivaroxaban in a mixture of a solvent and an antisolvent, wherein the antisolvent has a higher boiling point than the solvent;
(ii) removing the solvent by distillation; and
(iii) collecting the resultant rivaroxaban modification I.

It has been found that this process provides rivaroxaban modification I in a high yield and high purity without recourse to column chromatography or the use of acetic acid.

BRIEF DESCRIPTION OF THE DRAWINGS

The present invention will now be described with reference to the accompanying drawings, in which.

DETAILED DESCRIPTION OF THE INVENTION

Figure 1:
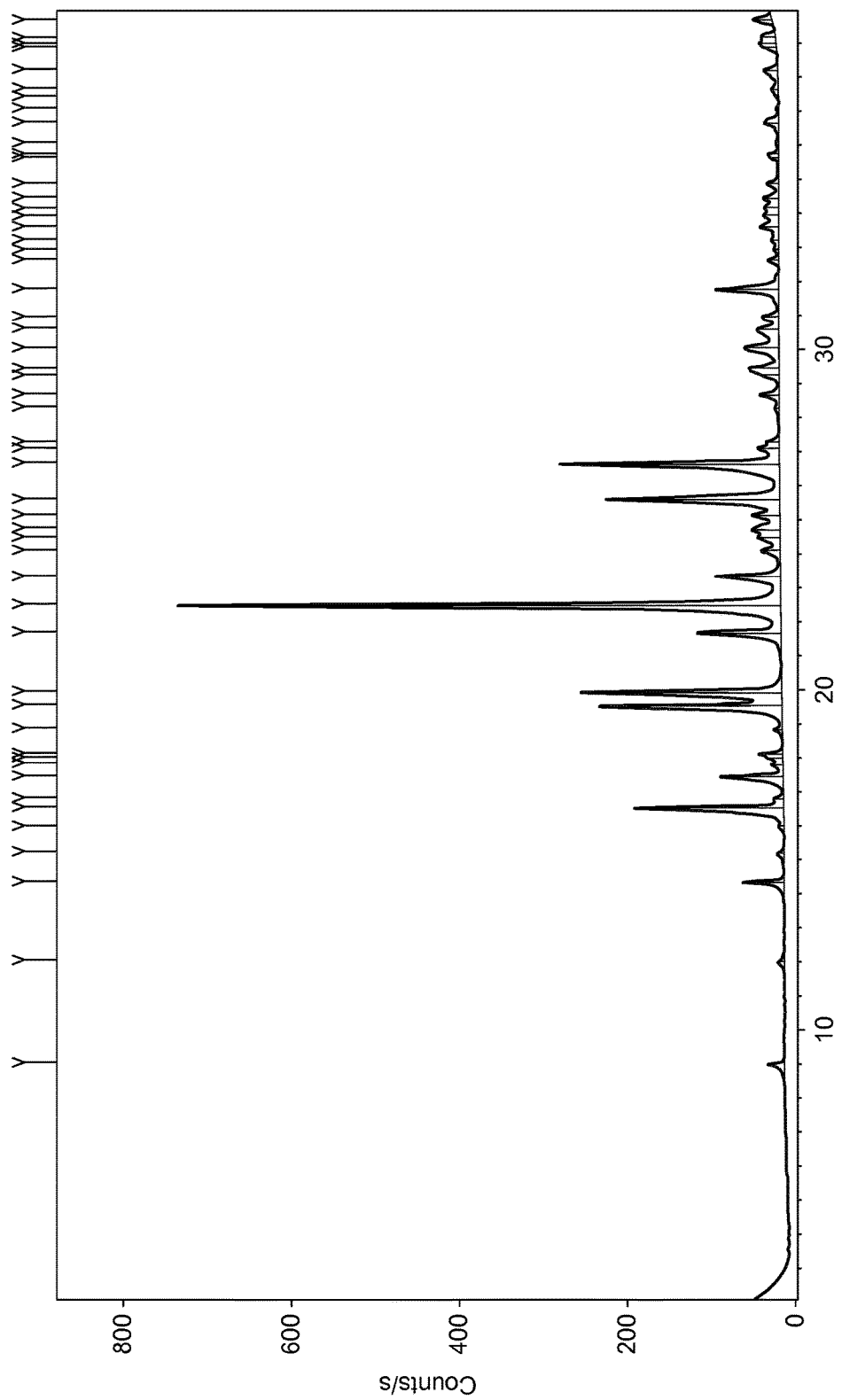
FIG. 1 shows the XRPD spectrum for the product of Example 1.

In step (i) of the present process, the rivaroxaban is dissolved in a mixture of a solvent and an antisolvent. The solvent preferably provides a solubility of at least 1 g rivaroxaban in 200 mL of solvent. The solubility may be determined at any point up to and including under reflux of the solvent, preferably under reflux. Suitable solvents include THF and/or acetone. The solvent is most preferably THF. To permit ready distillation, the solvent preferably has a boiling point at atmospheric pressure of less than (and not including) 100° C.

The antisolvent is preferably miscible with the solvent and must not be a solvent for rivaroxaban. That is, a solubility of less than 1 g in 200 mL solvent, which again may be determined at any point up to and including the reflux temperature of the solvent, preferably under reflux. Suitable antisolvents include toluene and/or water. Most preferably the antisolvent is a mixture of toluene and water. To permit distillation, the antisolvent must have a boiling point above that of the solvent when measured at the same pressure, e.g. atmospheric pressure. Preferably, the antisolvent or antisolvent mixture has boiling point at least 10° C. higher than the solvent or solvent mixture, when measured at the same pressure, e.g. atmospheric pressure. For the avoidance of doubt, atmospheric pressure is 101325 Pa.

To effect dissolution, the solvent/antisolvent mixture is preferably heated, and most preferably the solvent/antisolvent mixture is heated under reflux.

The lower limit of the ratio of rivaroxaban to solvent is set by the solubility of the rivaroxaban in the solvent at any given temperature. There should be a sufficient amount of solvent to dissolve the rivaroxaban. The solution may be heated, typically under reflux, to effect the dissolution. The upper limit is less important, but the amount of solvent is preferably kept to a minimum for economic reasons. In a preferred embodiment of the present invention, the solvent is THF and the ratio of rivaroxaban to THF is 1:50-200 w/v, more preferably 1:95-110 w/v, most preferably 1:100 w/v.

In another preferred embodiment, the solvent is THF and the antisolvent is a mixture of toluene and water. Preferably the ratio of THF to the mixture of toluene and water is 5:1 to 1:1 v/v.

Ideally, the solvent is THF, the antisolvent is a mixture of toluene and water, and the ratio of rivaroxaban to THF to toluene to water is 1 to 50-200 to 10-50 to 10-50 w/v/v/v. The most preferred ratio is 1:100:19:50 w/v/v/v.

In step (ii), the solvent is removed by distillation. In the distillation step, preferably at least 95% of the solvent is removed, more preferably all of the solvent is removed. After removal of the solvent, the mixture is cooled to room temperature (i.e. 20° C.), although it can be cooled lower, e.g. to 0° C.

In step (iii), the resultant rivaroxaban modification I is preferably collected by filtration. It is then typically washed with the antisolvent(s) and dried. The ratio of solvents in the distillate may be measured and the distillate recycled into the crystallisation process, with appropriate adjustments to the ratio of solvent/antisolvent if applicable.

The present process is straightforward and may proceed even with an impure source of rivaroxaban. Accordingly, the process includes an embodiment where the rivaroxaban has not been subjected to column chromatography. Indeed, the rivaroxaban may be provided as a starting material for the preparation process as crude rivaroxaban having an impurity content of up to 10% by weight, e.g. 0.10-10% by weight.

If any coloured impurities are present in the starting material, the solution of rivaroxaban may be treated with decolourising charcoal and then filtered to remove the charcoal.

Rivaroxaban is used for the treatment of thromboembolic diseases. The thromboembolic diseases are defined in more detail in WO 2007/039132. They include myocardial infarction with ST segment elevation (STEMI) and without ST segment elevation (non-STEMI), stable angina pectoris, unstable angina pectoris, reocclusions and restenoses after coronary interventions such as angioplasty or aortocoronary bypass, peripheral arterial occlusive diseases, pulmonary embolisms, deep vein thromboses and renal vein thromboses, transitory ischemic attacks, thrombotic and thromboembolic cerebral stroke, cerebral ischemias, stroke and systemic thromboembolisms and ischemias in patients with acute, intermittent or persistent cardiac arrhythmias, for example, atrial fibrillation, and those who are subject to cardioversion, furthermore in the case of patients with heart valve diseases or with artificial heart valves, disseminated intravasal clotting (DIC), microangiopathic hemolytic anemias, extracorporeal blood circulations, for example hemodialysis, and heart valve prostheses, atherosclerotic vascular diseases and inflammatory diseases such as rheumatic diseases of the locomotor system, Alzheimer's disease, inhibition of tumour growth and of metastasis formation, in microangiopathies, age-related macular degeneration, diabetic retinopathy, diabetic nephropathy and other microvascular diseases, and for the prevention and treatment of thromboembolic complications, for example, venous thromboembolisms, in tumour patients, in particular those who are subjected to relatively large surgical interventions or chemo/radiotherapy, the prevention of coagulation ex vivo, e.g. for the preservation of blood and plasma products, for the cleaning/pretreatment of catheters and other medical aids and equipment, for the coating of artificial surfaces of medical aids and equipment employed in vivo or ex vivo or in biological samples which contain factor Xa. It may also be used for the prevention of blood coagulation in vitro, in particular in blood preserves or biological samples which contain factor Xa.

Accordingly, the present invention also includes a process for preparing a rivaroxaban dosage form, comprising the steps of preparing rivaroxaban modification I as described herein and combining the rivaroxaban modification I with one or more pharmaceutically acceptable excipients. Rivaroxaban is typically administered orally and so the dosage form is preferably an oral dosage form, most preferably a tablet. In such a case, the process further comprises a tableting step. The oral dosage form may be a coated or uncoated tablet and may be prepared using standard techniques known in the art.

In the case of oral administration, the dose is usually 0.01 to 100 mg/Kg, preferably 0.01 to 20 mg/Kg and most preferably 0.1 to 10 mg/kg.

The present invention will now be described with reference to the following examples, which are not intended to be limiting.

EXAMPLES

Example 1

Rivaroxaban 13.5 g was added to 1,350 mL of THF. Water 675 mL and 250 mL of toluene were added and the mixture heated under reflux to dissolve the rivaroxaban. Activated charcoal was added. The ratio of rivaroxaban to THF to water to toluene was 1:100:50:18.75 w/v/v/v. The mixture was filtered and the THF was removed by distillation at 65-75° C. (which is between the boiling point of THF, 64-66° C., and that of the toluene/water azeotrope, 84° C. The rivaroxaban crystallised during the distillation process. The crystals were collected by filtration to provide 11.7 g rivaroxaban (yield 86.5%).

The crystalline rivaroxaban had a melting point of approximately 230° C. and an HPLC purity of 99.94%.

The sample was ground and XRPD was performed. The spectrum is shown in FIG. 1. The XRPD spectra were obtained using a PANalytical X'Pert PRO MPD diffractometer in Bragg-Brentano geometry, X'Celerator RTMS Detector. The apparatus used Cu K-alpha radiation (0.15418740 nm) with a scan range of 1.9990-40.0004° and a step size of 0.0167°.

The characterising diffraction lines are at 2θ (°): 16.5, 19.5, 22.5 and 23.4.

Figure 2:
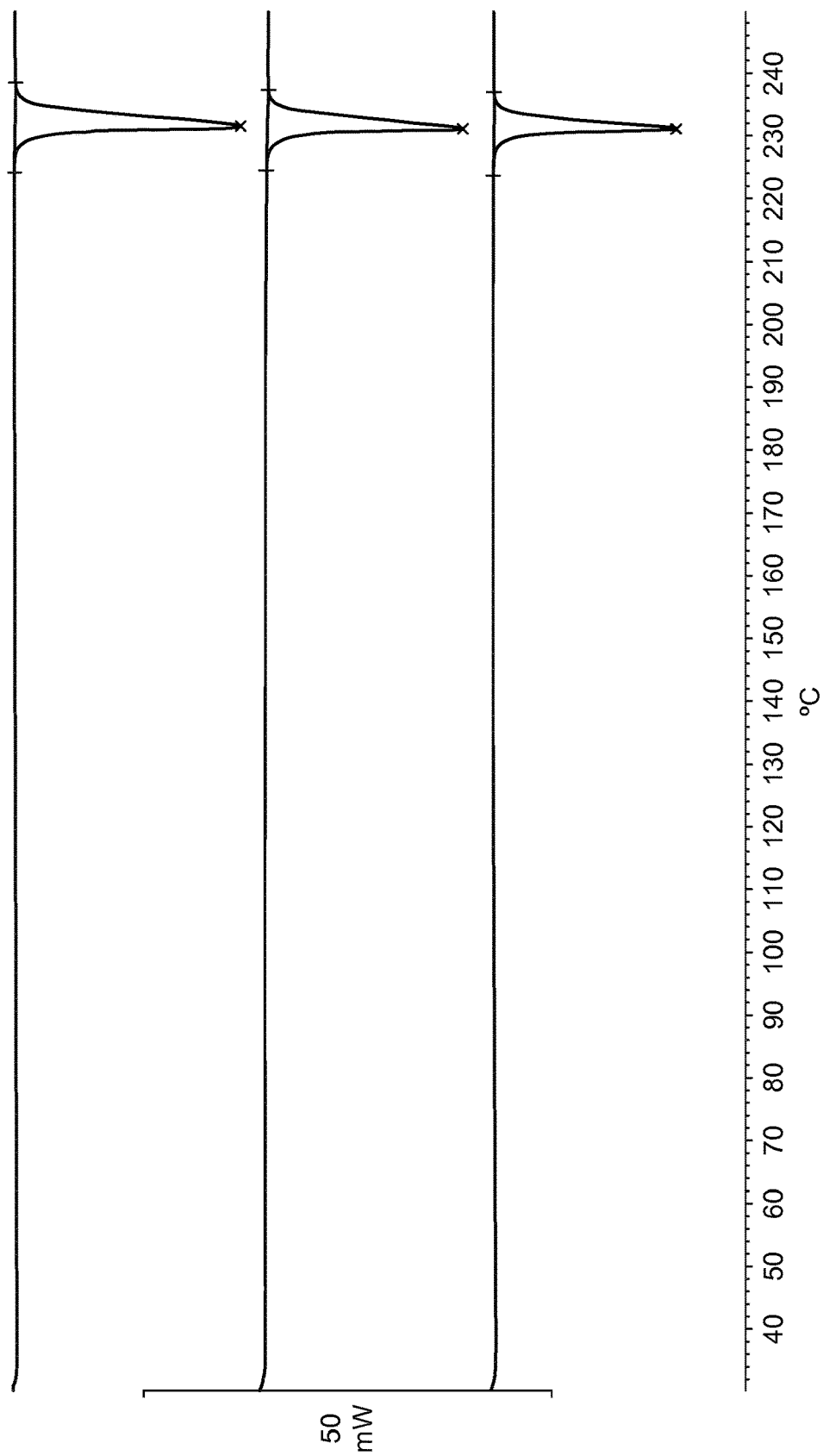
FIG. 2 shows the DSC traces for the product of Example 1.
Figure 3:
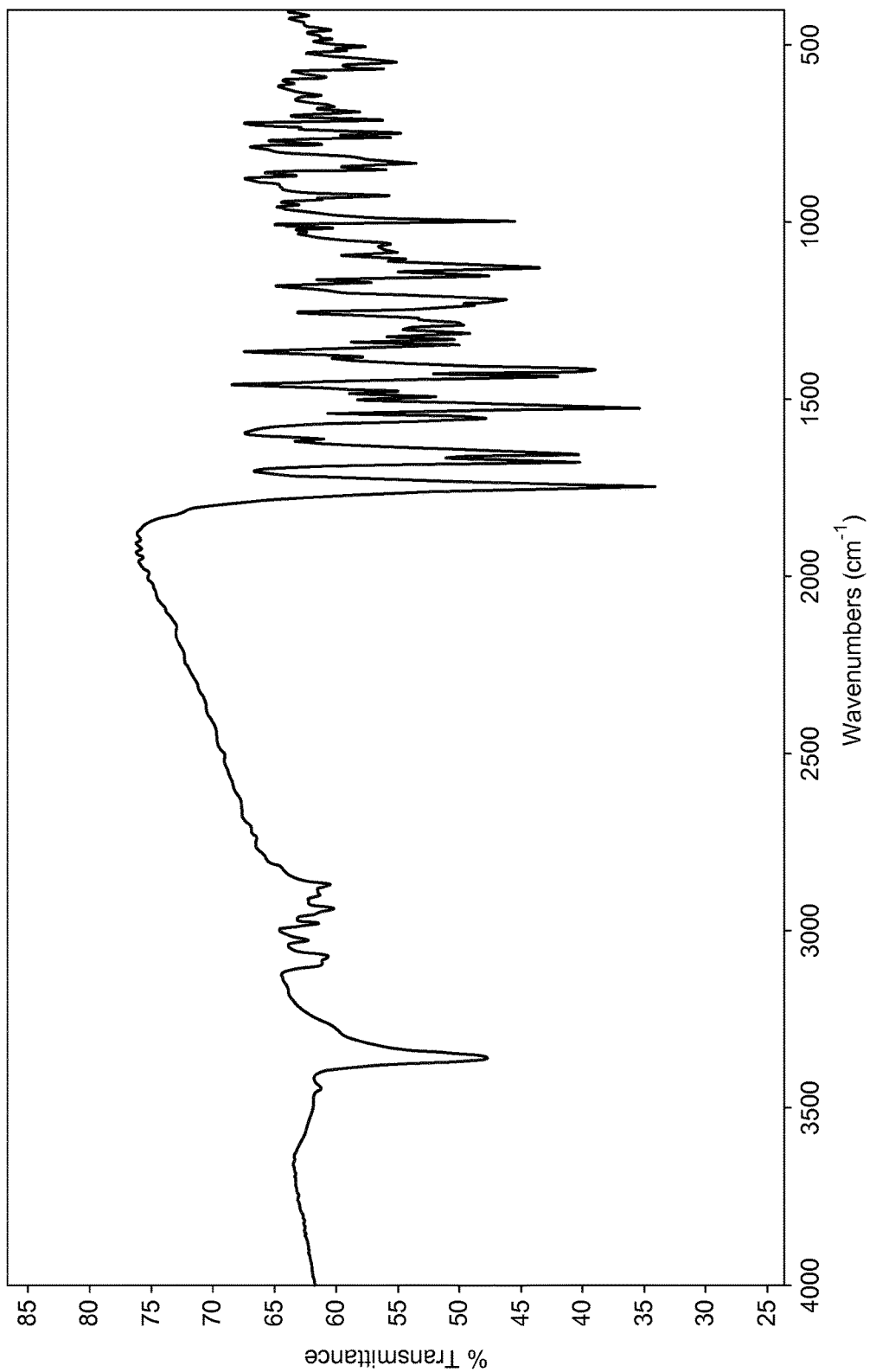
FIG. 3 shows the IR spectrum for the product of Example 1.

Differential scanning calorimetry (DSC) and infrared spectroscopy were also used and the DSC trace and IR spectrum are shown in FIGS. 2 and 3, respectively.

DSC was performed using a DSC822e Mettler-Toledo apparatus at a heating rate of 10.0° C./min.

The IR spectra were obtained according to Ph.Eur. (2.2.24.) and USP, <197K> using the KBr disc method. The apparatus was Avatar 370 FT-IR Thermo-Nicolet. The IR peak listing are at (cm$^{-1}$): 416, 455, 483, 501, 564, 587, 607, 640, 671, 685, 707, 731, 745, 756, 775, 813, 828, 846, 864, 920, 930, 946, 991, 1011, 1023, 1055, 1076, 1098, 1120, 1145, 1163, 1210, 1219, 1285, 1307, 1323, 1340, 1373, 1409, 1429, 1469, 1486, 1517, 1546, 1605, 1646, 1669, 1737, 2867, 2936, 2976, 3023, 3066, 3354 and 3442. The characteristic peaks are at (cm$^{-1}$): 564, 685, 707, 745, 756, 828, 846, 920, 991, 1011, 1055, 1076, 1120, 1145, 1163, 1219, 1285, 1307, 1323, 1340, 1373, 1409, 1429, 1469, 1486, 1517, 1546, 1605, 1646, 1669, 1737, 2867, 2936, 2976 and 3354.

Raman spectroscopy was also performed. The spectra were obtained using a Thermo Nicolet Almega XR. Spectra were consistent with modification I.

Example 2

Rivaroxaban 16 g was added to 1,600 mL of THF. Water 800 mL and 300 mL of toluene were added and the mixture heated under reflux to dissolve the rivaroxaban. The ratio of rivaroxaban to THF to water to toluene was 1:100:50:18.75 w/v/v/v. The procedure was then followed as set out in Example 1 to provide 13.5 g rivaroxaban (yield 84.4%).

Rivaroxaban modification I was characterised as set out for Example 1.

Examples 3-15

The procedure in Example 1 was repeated with different amounts of rivaroxaban, solvents and antisolvents. The results are set out in Table 1.

What is claimed is:

1. A process for the preparation of rivaroxaban modification I comprising:
   (i) dissolving rivaroxaban in a mixture of a solvent and an antisolvent, wherein the antisolvent has a higher boiling point than the solvent;
   (ii) removing the solvent by distillation; and
   (iii) collecting the resultant rivaroxaban modification I.

2. A process as claimed in claim 1, wherein the solvent is THF and/or acetone.

3. A process as claimed in claim 1, wherein the antisolvent is toluene and/or water.

4. A process as claimed in claim 1, wherein the solvent is THF and the antisolvent is a mixture of toluene and water.

5. A process as claimed in claim 1, wherein the solvent/antisolvent mixture is heated in step (i).

6. A process as claimed in claim 5, wherein the solvent/antisolvent mixture is heated under reflux.

7. A process as claimed in claim 5, wherein after removal of the solvent, the mixture is cooled to room temperature.

8. A process as claimed in claim 1, wherein the solvent is THF and the ratio of rivaroxaban to THF is 1:50-200 w/v.

TABLE 1

Figure 4:
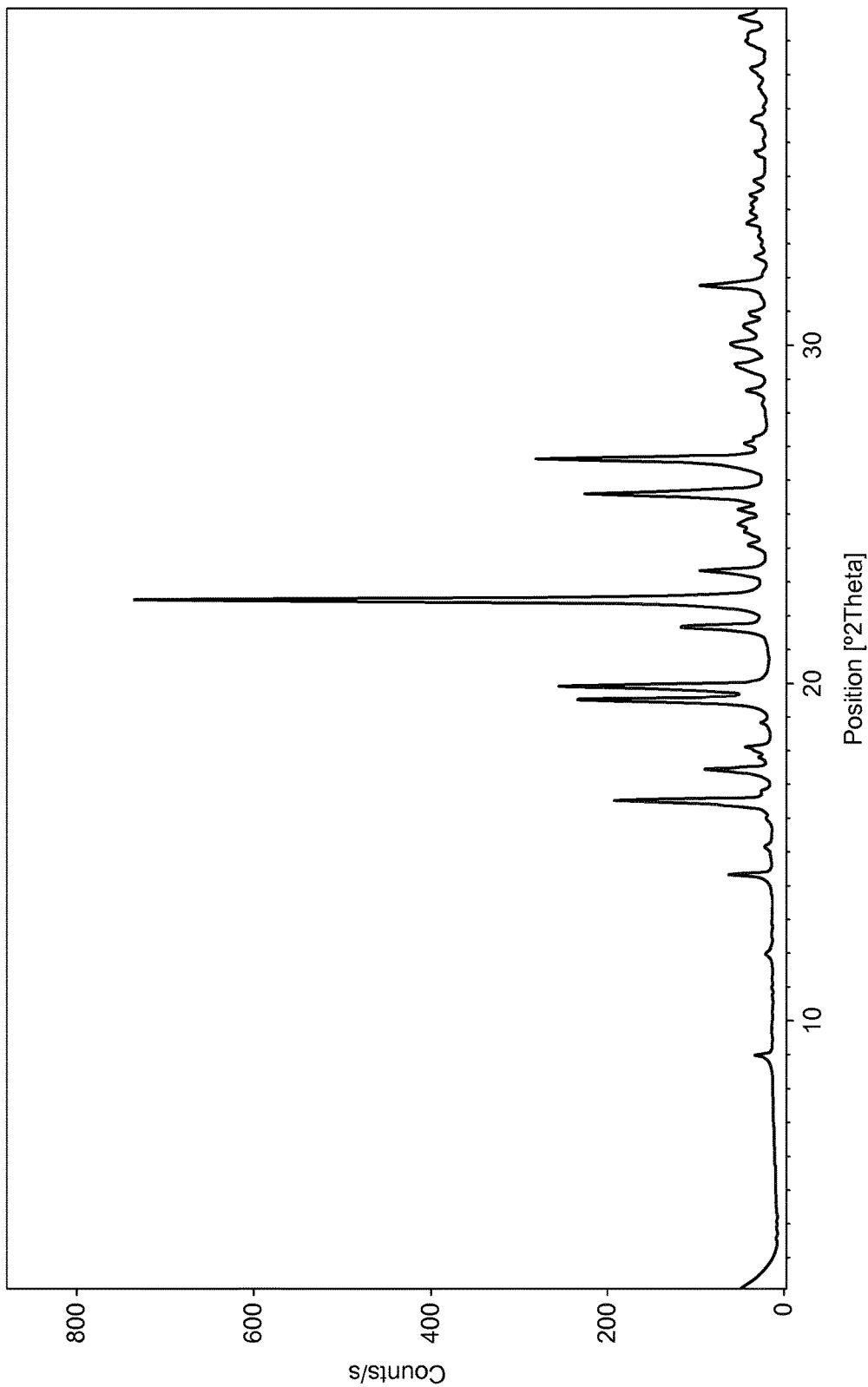
FIG. 4 shows an overlay of the XRPD spectra for the products of Examples 9 ("batch 390612") and 10 ("batch 470612").

| Ex. no. | Rivaroxaban (g) | Solvent (mL) | Yield (%) | HPLC purity (%) | Remarks |
| --- | --- | --- | --- | --- | --- |
| 3* | 1.5 | Dichloromethane, 200<br>Water, 30 | NA | 98.70 | Rivaroxaban insoluble in dichloromethane |
| 4* | 1.0 | Methanol, 200 | NA | 99.66 | Rivaroxaban insoluble in methanol |
| 5* | 1.0 | Toluene, 200 | NA | 97.93 | Rivaroxaban insoluble in toluene |
| 6 | 0.5 | Acetone, 200<br>Water, 50<br>Toluene, 50 | 71 | 99.82 | Modification I, according to XRPD |
| 7* | 0.5 | THF, 160 | 44 | 97.54 | XRPD not in accordance with modification I |
| 8* | 0.5 | Methyl-THF, 200 | NA | 98.17 | Rivaroxaban insoluble in Me-THF |
| 9 | 0.5 | THF, 50<br>Water, 25<br>Toluene, 25<br>(1/100/50/50) | 80 | 99.82 | Modification I, according to XRPD (see FIG. 4) |
| 10 | 2.0 | THF, 200<br>Water, 100<br>Toluene, 100<br>(1/100/50/50) | 90 | 99.75 | Modification I, according to XRPD (see FIG. 4) |
| 11 | 12 | THF, 1,200<br>Water, 600<br>Toluene 225<br>(1/100/50/18.75) | 75 | 99.82 | Modification I, according to XRPD |
| 12 | 14 | THF, 1,400<br>Water, 700<br>Toluene, 260<br>(1/100/50/18.6) | 100 | 99.88 | Modification I, according to XRPD |
| 13 | 8.0 | THF, 800<br>Water, 400<br>Toluene, 150<br>(1/100/50/18.75) | 81.30 | 99.70 | Modification I, according to XRPD |
| 14 | 8.0 | THF, 800<br>Water, 400<br>Toluene, 150<br>(1/100/50/18.75) | 83.39 | 99.74 | Modification I, according to XRPD |
| 15 | 8.0 | THF, 800<br>Water, 400<br>Toluene, 150<br>(1/100/50/18.75) | 87.40 | 99.76 | Modification I, according to XRPD |

*Comparative example, not of the invention

9. A process as claimed in claim 1, wherein the solvent is THF, the antisolvent is a mixture of toluene and water, and the ratio of THF to the mixture of toluene and water is 5:1 to 1:1 v/v.

10. A process as claimed in claim 1, wherein the solvent is THF, the antisolvent is a mixture of toluene and water, and the ratio of rivaroxaban to THF to toluene to water is 1 to 50-200 to 10-50 to 10-50 w/v/v/v.

11. A process as claimed in claim 1, wherein the resultant rivaroxaban modification I is collected by filtration.

12. A process as claimed in claim 1, wherein the rivaroxaban has not been subjected to column chromatography.

13. A process as claimed in claim 1, wherein the rivaroxaban is provided as a starting material for the preparation process as crude rivaroxaban having an impurity content of 0.10-10% by weight.

* * * * *